(12) United States Patent
Chong et al.

(10) Patent No.: US 8,918,168 B2
(45) Date of Patent: Dec. 23, 2014

(54) ELECTROCARDIOGRAM SIGNAL SENSING MODULE, APPARATUS AND COMPUTER TO BE INTEGRATED THEREWITH

(75) Inventors: Brian-Chua Chong, New Taipei (TW); Yao-Tsung Chang, New Taipei (TW); Chia-Hsien Li, New Taipei (TW); Pai-Yang Lin, New Taipei (TW); Shun-Chi Chung, New Taipei (TW)

(73) Assignee: Wistron Corp., New Taipei (TW)

( * ) Notice: Subject to any disclaimer, the term of this patent is extended or adjusted under 35 U.S.C. 154(b) by 0 days.

(21) Appl. No.: 13/425,337

(22) Filed: Mar. 20, 2012

(65) Prior Publication Data

US 2012/0245480 A1    Sep. 27, 2012

(30) Foreign Application Priority Data

Mar. 24, 2011  (TW) .............................. 100110088 A

(51) Int. Cl.
*A61B 5/04* (2006.01)
*A61B 5/0408* (2006.01)
*A61B 5/00* (2006.01)
*G06F 3/01* (2006.01)
*G06F 3/0354* (2013.01)
*G06F 19/00* (2011.01)
*A61B 5/021* (2006.01)
*A61B 5/16* (2006.01)

(52) U.S. Cl.
CPC ............. *A61B 5/0408* (2013.01); *A61B 5/6897* (2013.01); *G06F 3/011* (2013.01); *G06F 3/015* (2013.01); *G06F 3/03547* (2013.01); *G06F 19/3406* (2013.01); *A61B 5/021* (2013.01); *A61B 5/165* (2013.01); *G06F 2203/011* (2013.01)
USPC ........................................... 600/523; 600/519

(58) Field of Classification Search
CPC . A61B 5/0408; A61B 5/6897; G06F 3/03547
USPC ........................................................ 600/523
See application file for complete search history.

(56) References Cited

U.S. PATENT DOCUMENTS 4,535,783 A *   8/1985   Marangoni .................. 600/524
7,149,571 B2    12/2006  Maeda
(Continued)

FOREIGN PATENT DOCUMENTS

CN        1419888       5/2003
TW        I308708       4/2009

OTHER PUBLICATIONS

Taiwanese language office action dated May 15, 2013.
(Continued)

*Primary Examiner* — Michael Kahelin
*Assistant Examiner* — Mallika D Fairchild
(74) *Attorney, Agent, or Firm* — McClure, Qualey & Rodack, LLP

(57) ABSTRACT

An electrocardiogram (ECG) signal sensing module is provide. The ECG signal sensing module includes at least one touchpad button, for producing a press signal when being pressed; at least one sensing electrode, mounted on the at least one touchpad button and moving in unison with the at least one touchpad button, for measuring the voltage on the portion thereof touched by a user; an electrocardiogram signal processor, coupled to the at least one sensing electrode, for processing the voltage on the at least one sensing electrode and producing an ECG signal; and a transmission interface, coupled to the at least one touchpad button and the electrocardiogram signal processor, for outputting the press signal and the ECG signal to a computer.

11 Claims, 10 Drawing Sheets

(56) References Cited

U.S. PATENT DOCUMENTS

2003/0097078 A1* 5/2003 Maeda .................... 600/509
2009/0259134 A1* 10/2009 Levine .................... 600/523

OTHER PUBLICATIONS

English language translation of relevant paragraphs of office action.
English language translation of relevant paragraphs of TW I308708 (published Apr. 11, 2009).
Taiwanese language office action dated Nov. 20, 2013.
English language translation of relevant paragraphs from Taiwan OA.
Chinese language office action dated Nov. 20, 2013.
English language translation of relevant paragraphs from Chinese OA.
Taiwanese language office action dated Jun. 4, 2014.
English language translation of relevant paragraphs of Taiwan office action.

* cited by examiner

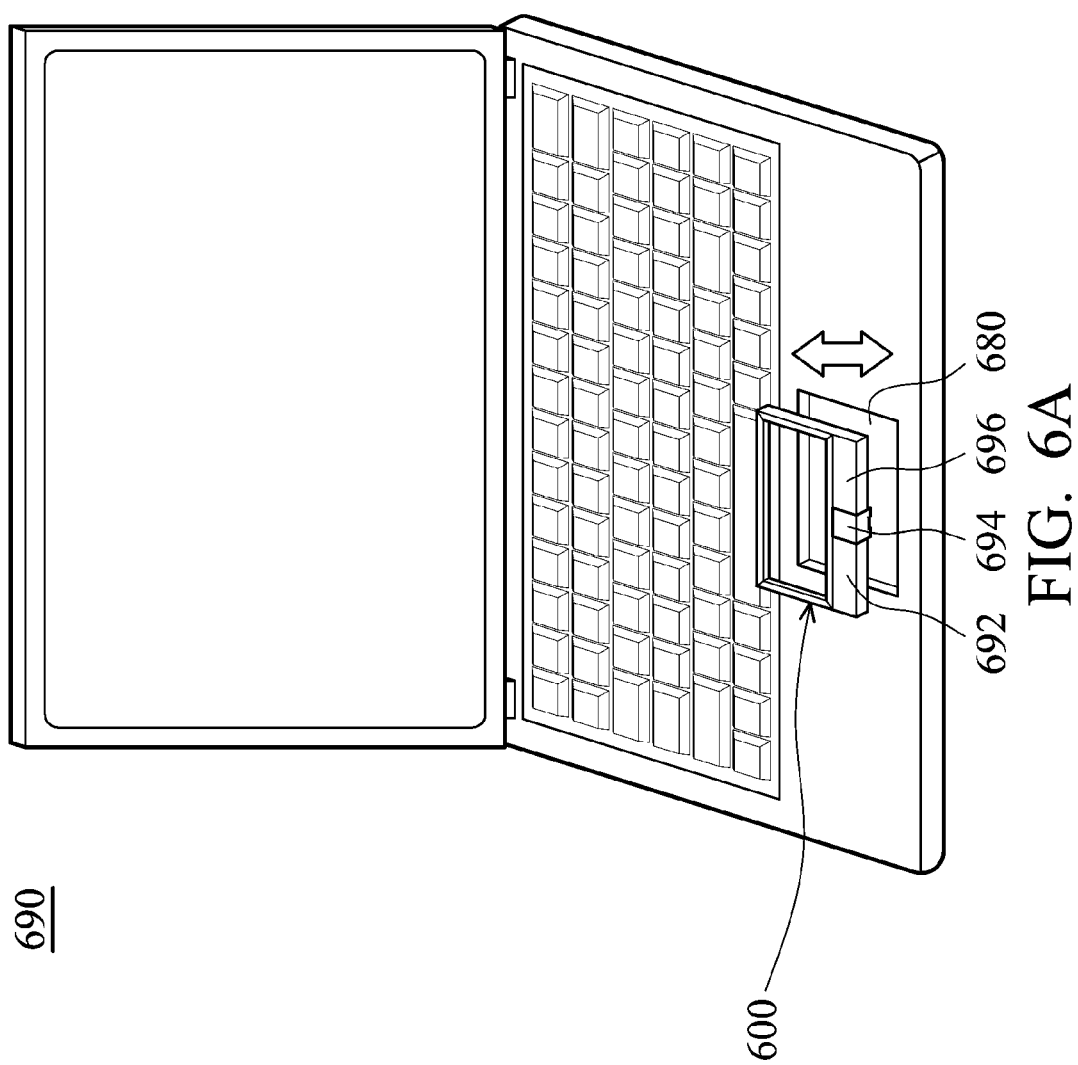

ELECTROCARDIOGRAM SIGNAL SENSING MODULE, APPARATUS AND COMPUTER TO BE INTEGRATED THEREWITH

CROSS REFERENCE TO RELATED APPLICATIONS

This Non-provisional application claims priority under 35 U.S.C. §119(a) on Patent Application No(s). 100110088, filed in Taiwan, Republic of China on Mar. 24, 2011, the entire contents of which are hereby incorporated by reference.

BACKGROUND OF THE INVENTION

1. Field of the Invention

The present invention relates to the measurement of an electrocardiogram (ECG) signal, and in particular relates to the integration of an ECG signal sensing apparatus and an electric device, such as a touchpad of a notebook.

2. Description of the Related Art

Cardiac health, in tradition, is usually examined by using a professional electrocardiogram (ECG) machine in a hospital or clinic. The professional ECG machine have several electrodes (usually 12), and each electrode has to be attached to the body by skilled medical person. Operating the ECG machine is a specialized job, and most people do not use it to examine cardiac health at home.

There is a portable handheld ECG machine which provides another way to obtain an ECG signal. Limited by its size, this kind of ECG machine usually has only two electrodes, and thus has poorer precision than the professional one. Since a portable ECG machine increases convenience for use, it has gradually become popular in household health care. However, those generally healthy people who are not elder and have no chronic disease, will not purposely buy or use the portable ECG machine and adapt it to care for their health.

Since computers have become a daily necessity, it will be beneficial for one's health, if physical condition can be monitored when using the computer.

BRIEF SUMMARY OF THE INVENTION

The present invention provides an electrocardiogram (ECG) signal sensing module. The ECG signal sensing module comprises at least one touchpad button, for producing a press signal when being pressed; at least one sensing electrode, mounted on the touchpad button and moving in unison with the touchpad button, for measuring the voltage on the portion of a user touching the touchpad button; an electrocardiogram signal processor, coupled to the sensing electrode, for processing the voltage on the sensing electrode and producing an ECG signal; and a transmission interface, coupled to the touchpad button and the electrocardiogram signal processor, for outputting the press signal and the ECG signal to a computer.

The present invention also provides an electrocardiogram signal (ECG) sensing apparatus. The ECG signal sensing apparatus comprises at least one button, for engaging and moving in unison with a touchpad button, for pressing the touchpad button indirectly when being pressed; at least one sensing electrode, mounted on the button, for measuring the voltage on the portion of a user touching the button; an electrocardiogram signal processor, coupled to the sensing electrode, for processing the voltage on the sensing electrode and producing an ECG signal; and a transmission interface, coupled to the electrocardiogram signal processor, for outputting the ECG signal to a computer.

The present invention also provides a computer, which comprises a touchpad area for being assembled and engaging with the electrocardiogram signal sensing apparatus above.

The present invention also provides a computer, which comprises an electrocardiogram signal sensing module comprising: a touch sensor, for producing a touch signal when being pressed; at least one touchpad button, for producing a press signal when being pressed; at least one sensing electrode, mounted on the touchpad button and moving in unison with the touchpad button, for measuring the voltage on the portion of a user touching the button; and an electrocardiogram signal processor, coupled to the sensing electrode, for processing the voltage on the sensing electrode and producing an ECG signal.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIG. 6A is a schematic diagram of the electrocardiogram signal sensing apparatus according to an embodiment of the present invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
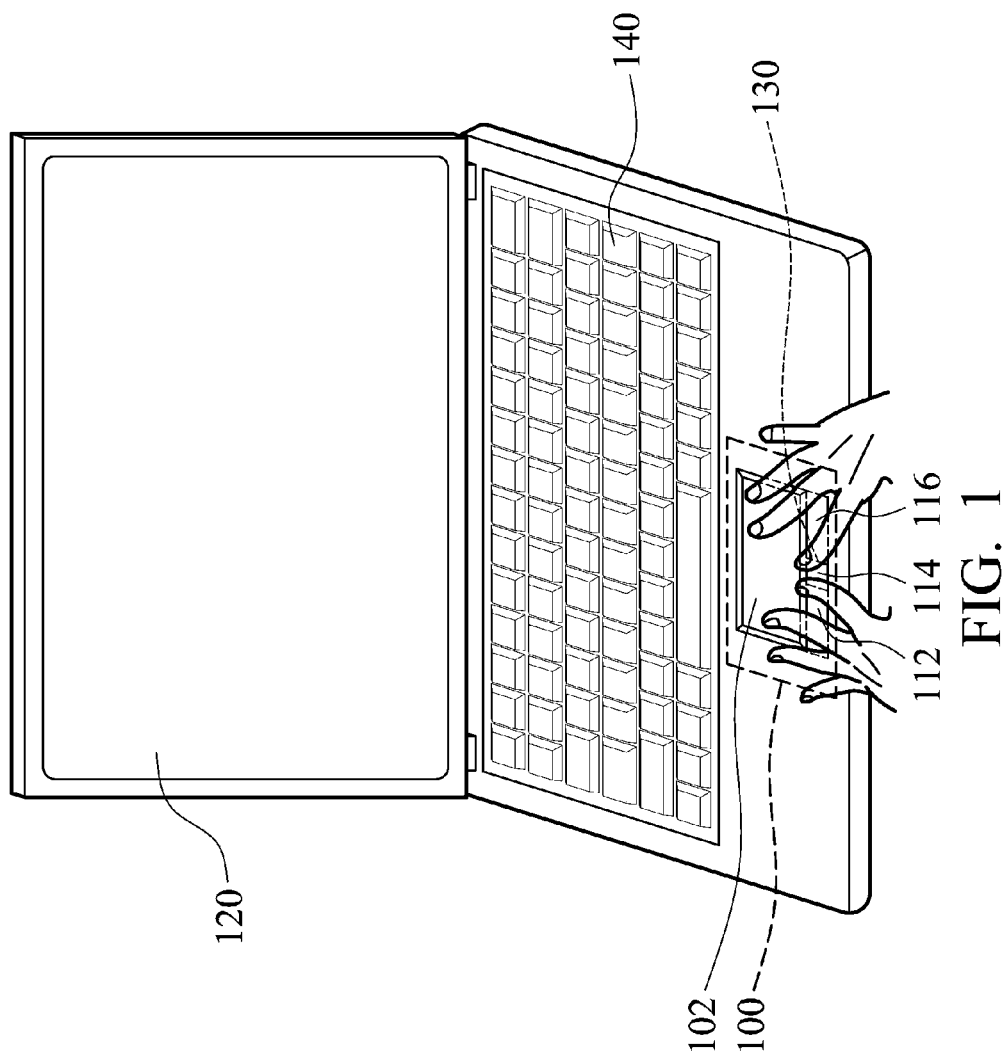
FIG. 1 is a schematic diagram of a touchpad in a notebook computer of the prior art.

FIG. 1 is a schematic diagram of a touchpad in a notebook computer of the prior art. The touchpad area 100 in the notebook computer is usually beneath the keyboard area 140, and comprises a touch sensor 102, touchpad buttons 112, 114 and 116, and a touchpad controller (not shown). The touch sensor 102 has two electrical conductive layers including one x layer and one y layer. When a user touches the surface of the touch sensor 102 with a finger 130 or a stylus, the touchpad controller can determine the location of the part the user touches through the two electrical conductive layers and thus control the movement of the cursor on the screen 120 of the notebook computer. In the embodiment of FIG. 1, the three touchpad buttons: left touchpad button 112, middle touchpad button 114, and right touchpad button 116, are all at the lower edge of the touch sensor 102. In general, these three touchpad buttons, when being pressed, function as the left, middle and right buttons of a conventional computer mouse. The present invention, for illustration, is in the shape of and serves as the touchpad area 100 of a notebook computer of the prior art in the embodiment of FIG. 1, however, those skilled in the art should understand that the present invention does not limited to be used on the notebook computer but can be used on an external touchpad or any electronic device which has a touchpad area disposed thereon. The electrocardiogram signal sensing module of the present invention which can be independently used as a touchpad and the electrocardiogram signal sensing apparatus of the present invention which can be assembled with a touchpad, both will be further described in the following embodiments.

《The Electrocardiogram Signal Sensing Module which can be Independently Used as a Touchpad》

Figure 2A:
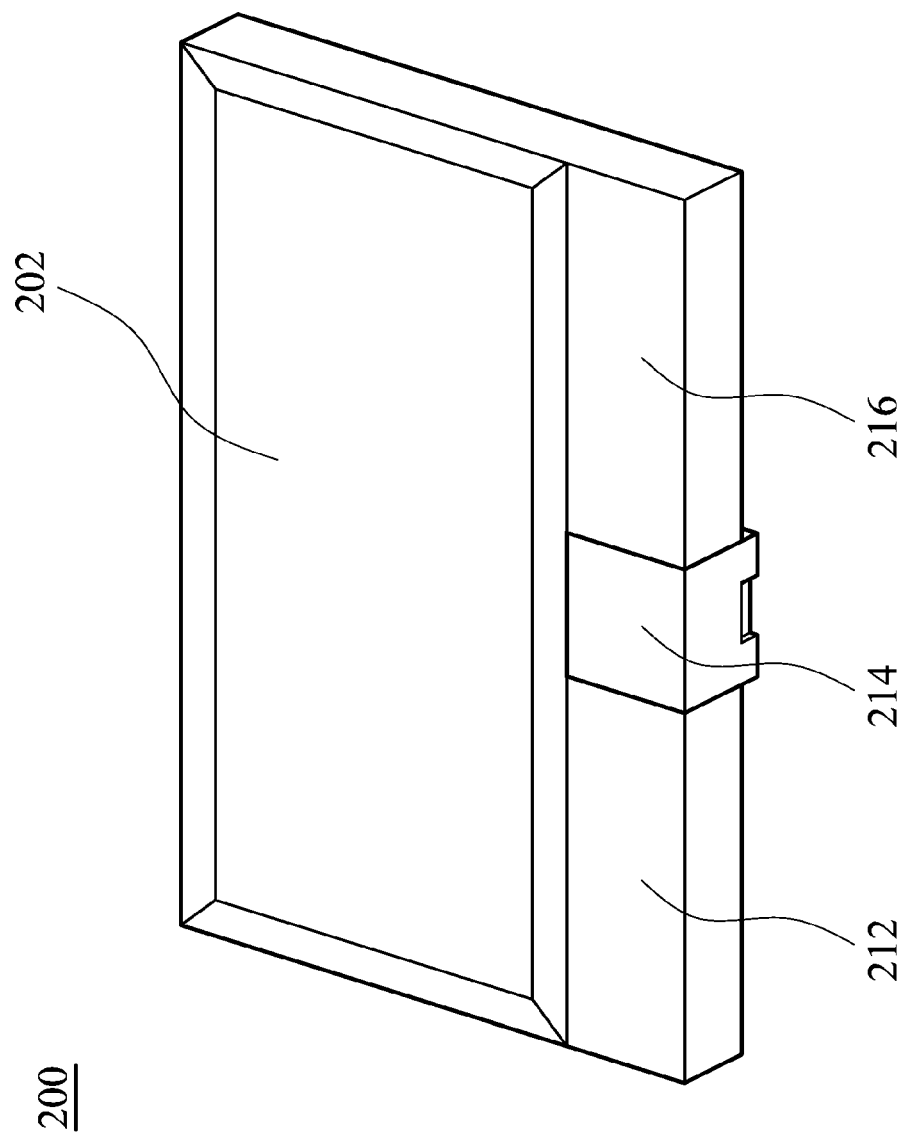
FIG. 2A is a schematic diagram of the electrocardiogram signal sensing module according to an embodiment of the present invention.
Figure 2B:
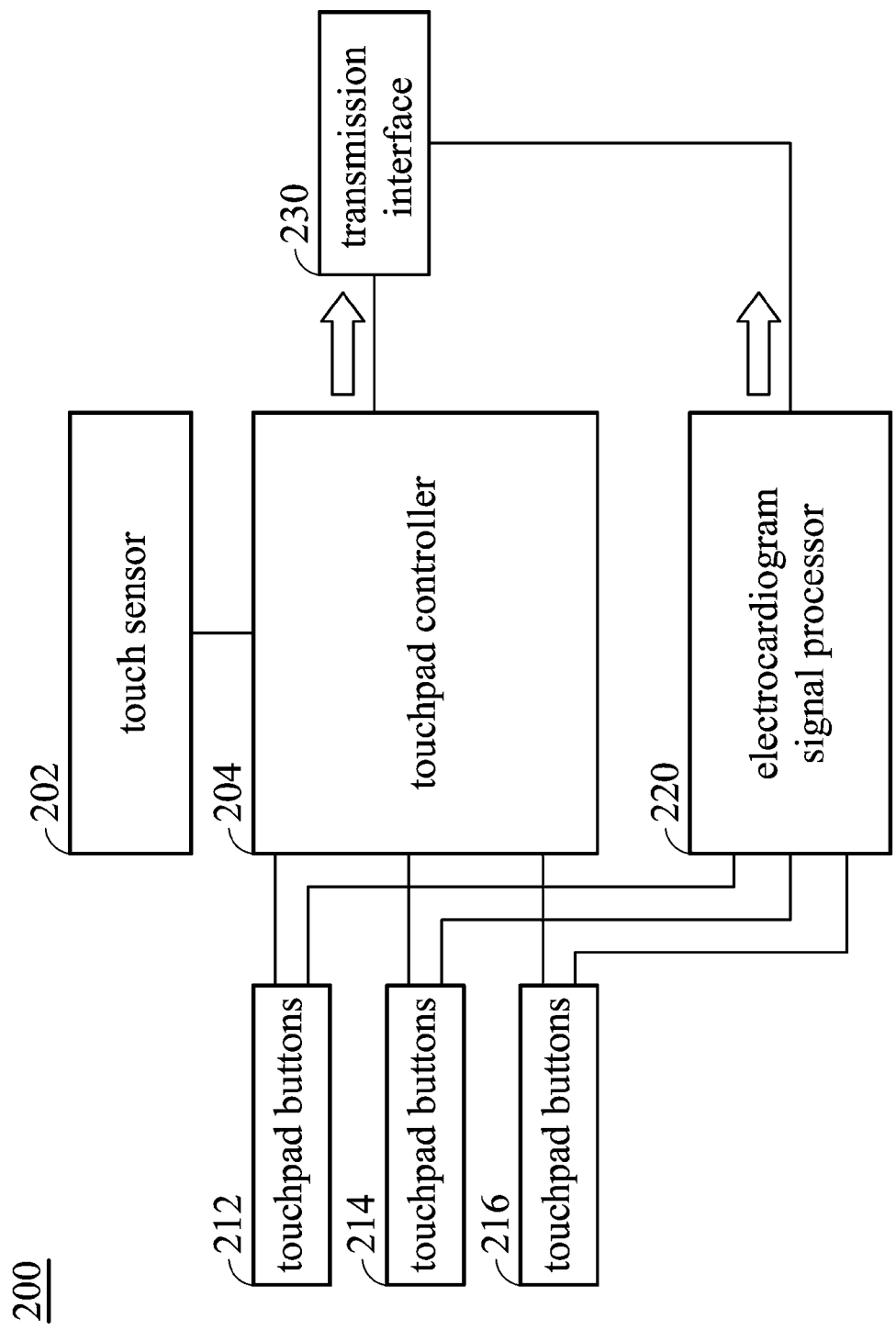
FIG. 2B shows the functional blocks of the electrocardiogram signal sensing module according to an embodiment of the present invention.

FIG. 2A is a schematic diagram of the electrocardiogram signal sensing module according to an embodiment of the present invention, and FIG. 2B shows the functional blocks of the electrocardiogram signal sensing module according to an embodiment of the present invention. In this embodiment, the electrocardiogram signal sensing module 200 can be either fixedly disposed on the notebook computer, for example, disposed at the lower edge of the keyboard 140 as shown in FIG. 1, or, disassembled from the notebook computer and operated independently. Referring to FIGS. 2A and 2B, the same as the touchpad area of a common notebook computer, the electrocardiogram signal sensing module 200 of the present invention has a touch sensor 202, at least one touchpad button (in the embodiment of FIG. 2, there are three touchpad buttons: left touchpad button 212, middle touchpad button 214, and right touchpad button 216) and a touchpad controller 204. The touch sensor 202 can produce a touch signal when being touched by the user, and each of the touchpad buttons 212~216 can produce a press signal when being pressed. The touch signal and the press signal will be transmitted to the touchpad controller 204 for signal processing. For example, the touch signal may be analyzed by the touchpad controller 204 to determine the position where the user touches the electrocardiogram signal sensing module 200 for controlling the motion of a cursor on a screen.

Figure 3:
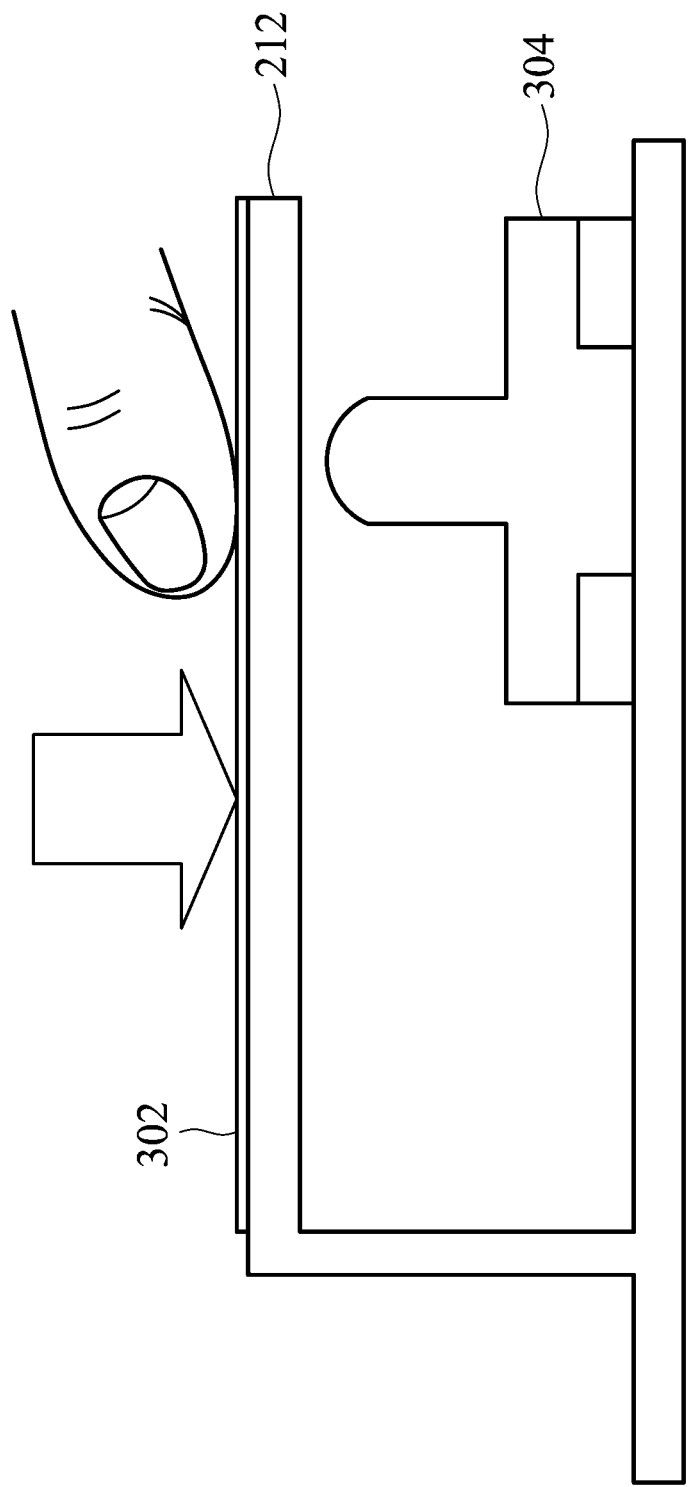
FIG. 3 shows the combination of the sensing electrode 302 and touchpad button 212.

In particular, the present invention further comprises several sensing electrodes. In the embodiment of FIGS. 2A and 2B, there are three sensing electrodes: left sensing electrode, middle sensing electrode and right sensing electrode, which are respectively disposed on and can move in unison with the left, middle, and right touchpad buttons 212~216. FIG. 3 shows the combination of the sensing electrode 302 and touchpad button 212. In FIG. 3, the touchpad button 212 physically includes an electric switch 304, which output two electrical states (e.g., "0" or "1") according to whether it is being pressed. As can be seen from FIG. 3, the sensing electrode 302 of the touchpad button 212 is located above the respective electric switch 304, and may be made of conductive material such as silver compounds (for example, silver chloride), or stainless steel. When a user presses the touchpad button 212, the sensing electrode 302 can simultaneously measure the voltage of the portion of the touchpad button 212 where the user touches. For example, in FIGS. 2A and 2B, when the user respectively uses a left hand finger and a right hand finger to touch the left touchpad button 212 and the right touchpad button 216, the left and right sensing electrodes respectively detects the slight voltage variation of a skin of the left and right hand fingers. Since the middle button of a traditional mouse is less commonly used, the middle sensing electrode of the present invention, in this manner, can be designed to be grounded. Then, the voltage sensed by the sensing electrode will be further sent to the electrocardiogram signal processor 220 which is coupled to the sensing electrodes 212~216 for signal processing. The electrocardiogram signal processor 220 coupled to the sensing electrodes 212~216 further processes (e.g., filters and amplifies) the detected voltage and produces an electrocardiogram (ECG) signal. By measuring the voltage difference between the right and left hands, the initiation and upshoot of the action potential between two sides of the cardiac muscle can be deduced. The electrocardiogram signal processor 220 discussed above can not only obtain the electrocardiogram of the user from the ECG signal, but may also deduce the blood pressure or heart beat rate, estimate the mood or stress model of users and even perform a lie detection test for the user. The present invention can be used for various purposes.

Figure 4A:
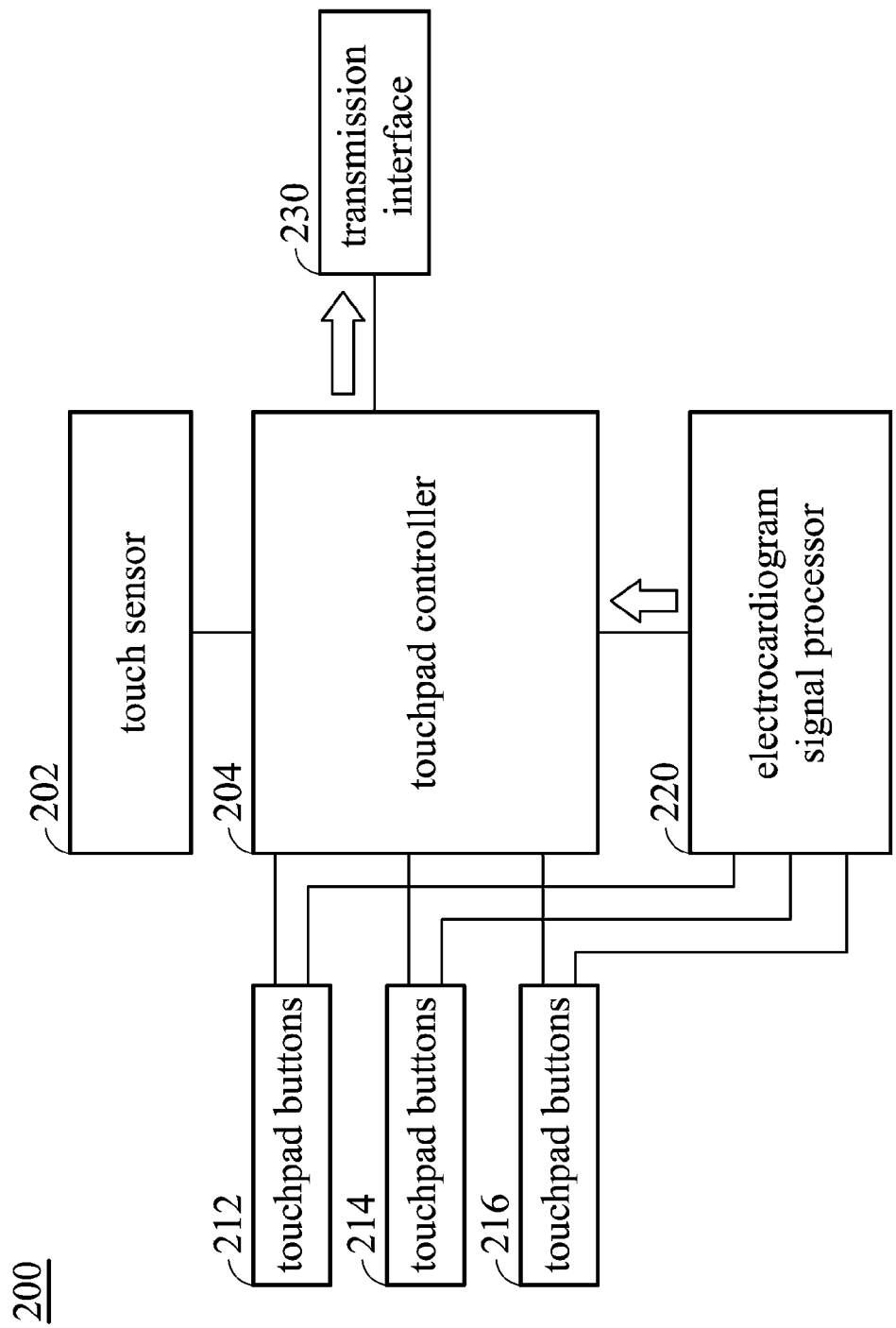
FIGS. 4A and 4B show two transmission interfaces, which are respectively connected to other components of the present invention in two fashions.
Figure 4B:
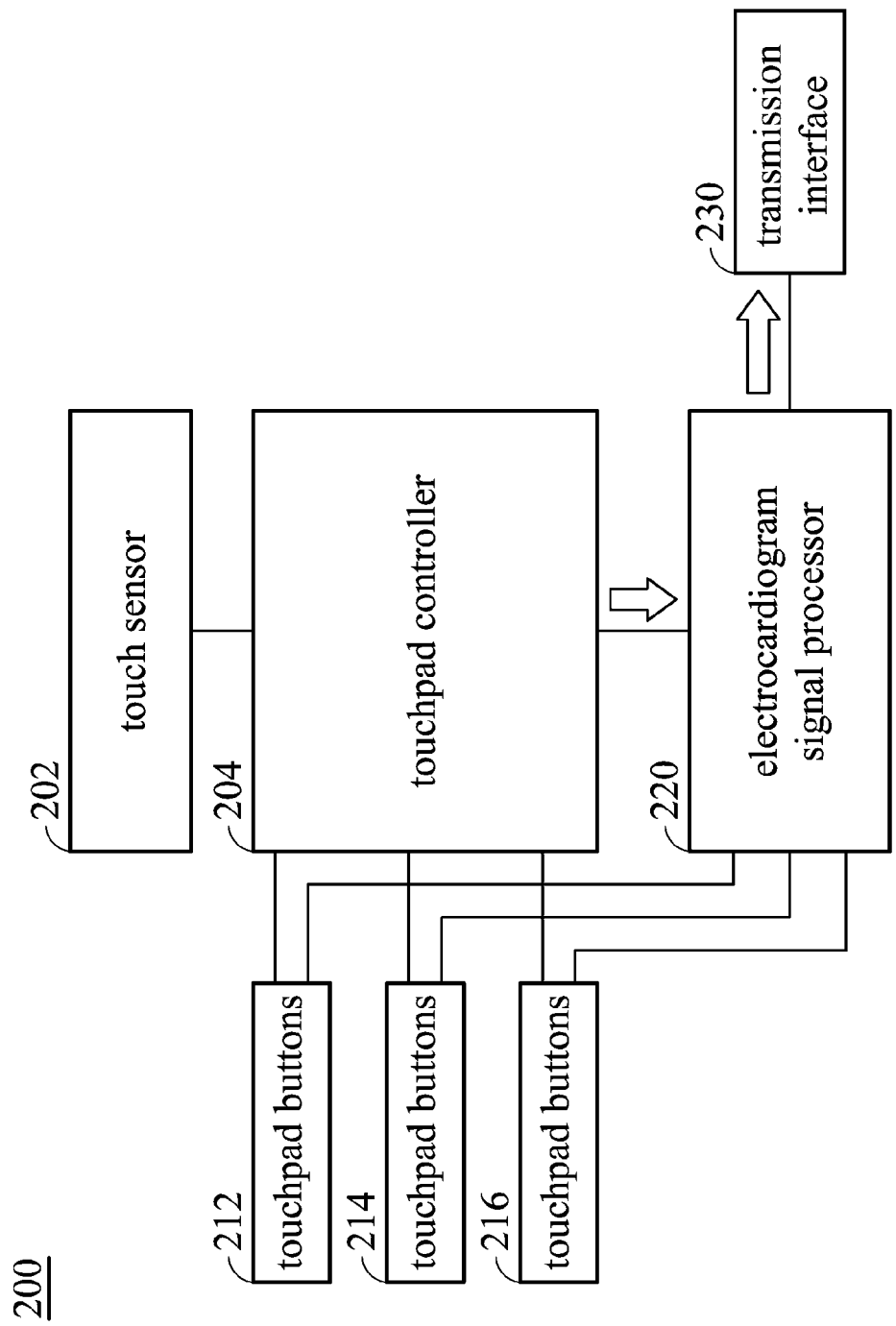

In addition, the electrocardiogram signal sensing module 200 of the present invention further comprises a transmission interface 230. By using the transmission interface 230, the touch signal produced by the touch sensor 202, the press signal produced by the touchpad button 212~216 and the ECG signal produced by the electrocardiogram signal processor 220 will be outputted to a computer which is connected with the electrocardiogram signal sensing module 200 of the present invention, either through wire or wireless means. The transmission interface 230 of the present invention is coupled (connected directly or indirectly) to the touch sensor 202, the touchpad button 212~216 and the electrocardiogram signal processor 220. FIGS. 4A and 4B show two transmission interfaces, which are respectively connected to other components of the present invention in two fashions. In FIG. 4A, the transmission interface 230 is coupled to the touchpad controller 204, and the ECG signal produced by the electrocardiogram signal processor 220 is sent to the transmission interface 230 through the touchpad controller 204. In FIG. 4B, the transmission interface 230 is coupled to the electrocardiogram signal processor 220, and the touch signal produced by the touch sensor 202 and the press signal produced by the touchpad button 212~216 are sent to the transmission interface 230 through the electrocardiogram signal processor 220. The transmission interface 230 of the present invention may comprise a wired transmission interface which, for example, uses a USB or $I^2C$ communication protocol, a wireless transmission interface which, for example, uses Bluetooth or wireless USB protocol, or the combination of the wired and wireless transmission interface.

Figure 5A:
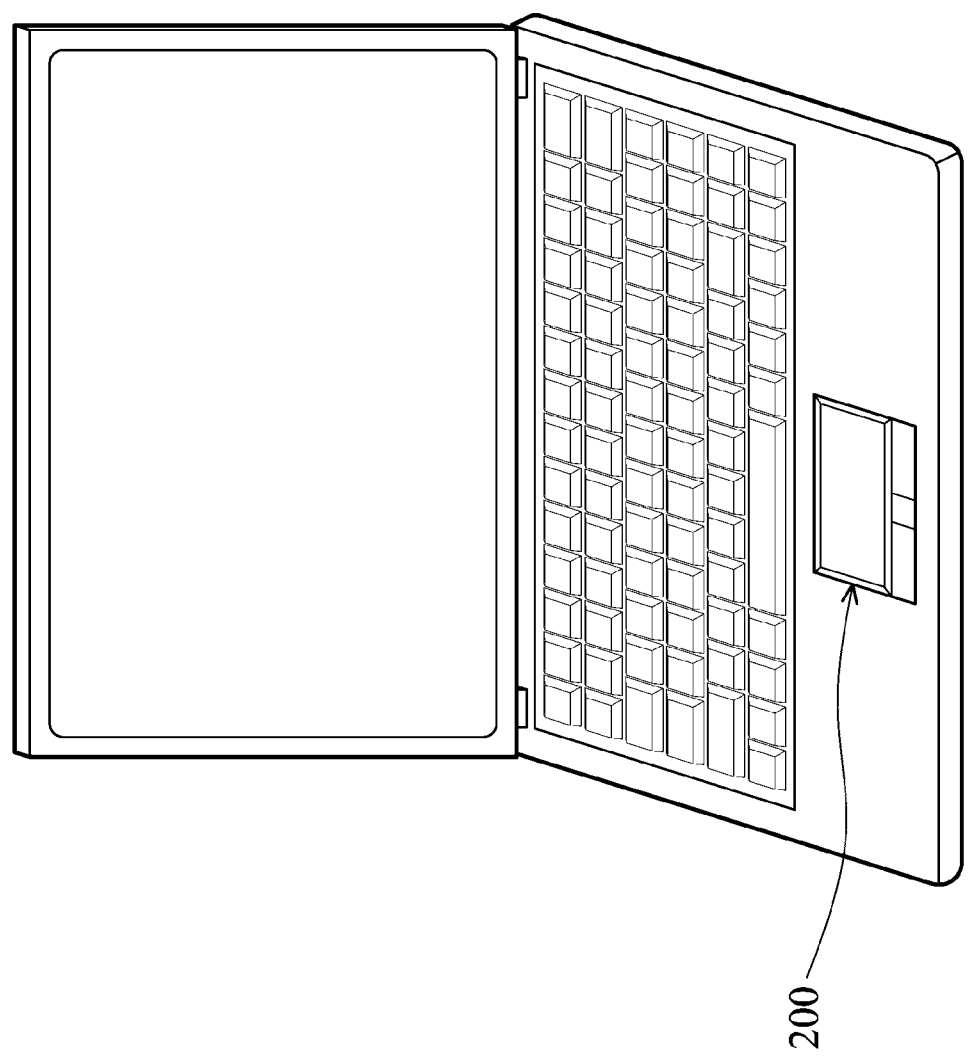
FIG. 5A shows an electrocardiogram signal sensing module which is engaged with the notebook.
Figure 5B:
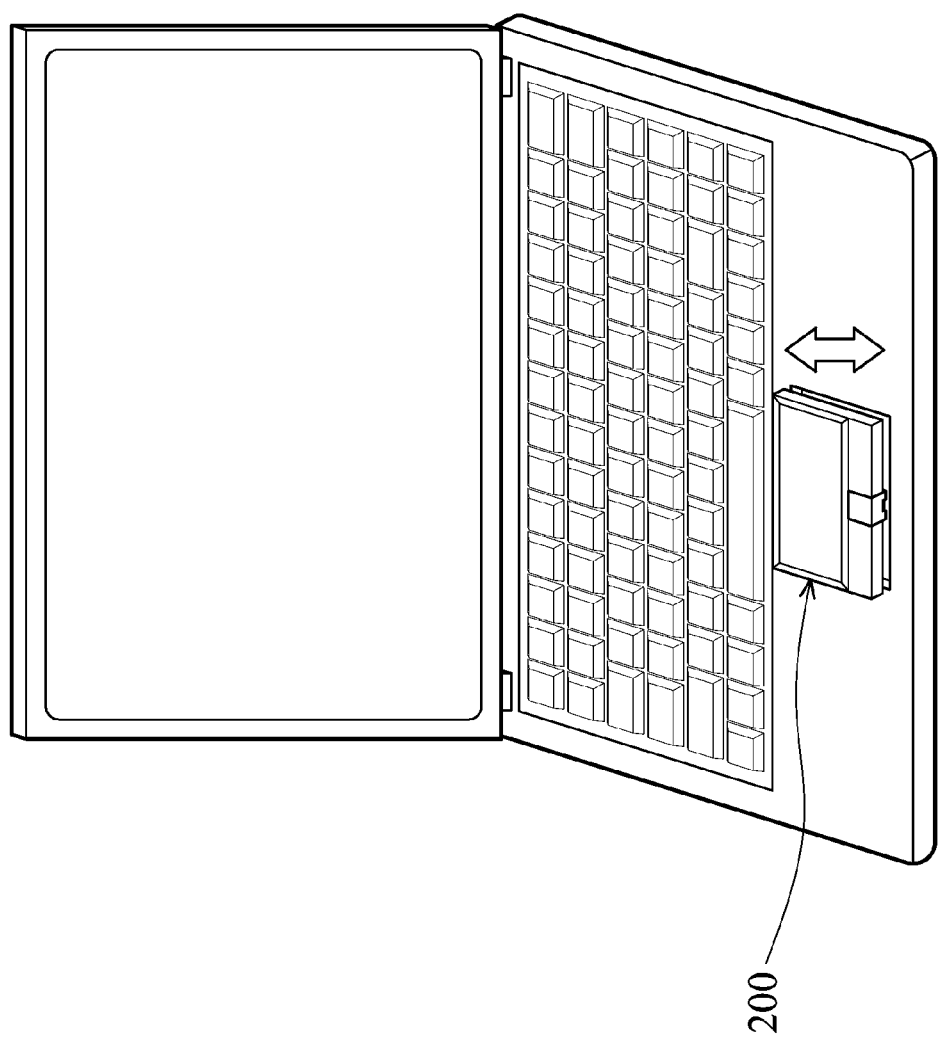
FIG. 5B shows an electrocardiogram signal sensing module 200 which is separated from the notebook computer.

It should be noted that the electrocardiogram signal sensing module 200 can be fixedly configured to the computer and mainly function as a general touchpad, or can operate independently mainly for sensing the ECG signal. FIG. 5A shows an electrocardiogram signal sensing module which is engaged with the notebook, and FIG. 5B shows an electrocardiogram signal sensing module 200 which is separated from the notebook computer.

In some embodiments, the touch sensor 202 can be further replaced by a touchpad screen (not shown in Figs.). In addition to performing as a touchpad, the touchpad screen can display the electrocardiogram corresponding to the ECG signal and information related to the ECG signal, such as the blood pressure, heart beat rate, mood or stress model of a user, at the same time.

In some embodiments, the present invention comprises a computer which is used to fixedly configure the electrocardiogram signal sensing module 200 described above. In some other embodiments, the touch sensor 202 can be removed from the electrocardiogram signal sensing module 200, and users can directly use the existing touch sensor of a computer with which the electrocardiogram signal sensing module 200 of the present invention is assembled. Those skilled in the art may modify the present invention according to the described embodiments. The concept for assembling the present invention with a computer will be further discussed in the following.

《The Electrocardiogram Signal Sensing Apparatus which can be Assembled with a Touchpad》

Figure 6B:
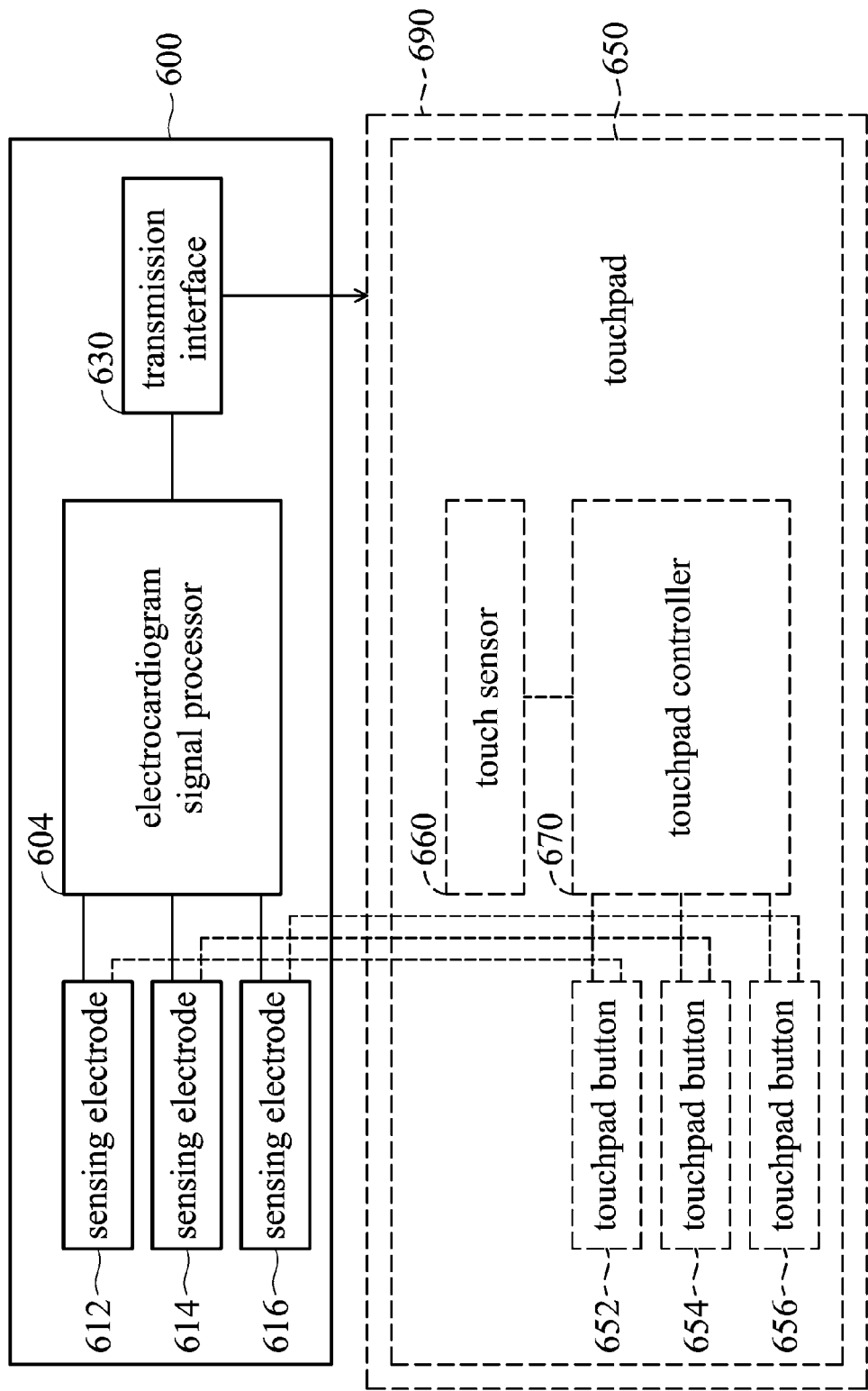
FIG. 6B is the functional blocks of the electrocardiogram signal sensing apparatus in FIG. 6A.

In addition to the electrocardiogram signal sensing module 200, the present invention further provides an electrocardiogram signal sensing apparatus. FIG. 6A is a schematic diagram of the electrocardiogram signal sensing apparatus according to an embodiment of the present invention; and FIG. 6B is the functional blocks of the electrocardiogram signal sensing apparatus according to an embodiment of the present invention. In an embodiment, the main purpose of the electrocardiogram signal sensing apparatus 600 is to sense the ECG signal. The electrocardiogram signal sensing apparatus 600 comprises sensing electrodes 612, 614 and 616 which are similar to those described in the previous embodiments; an electrocardiogram signal processor 604 and a transmission interface 630. The sensing electrodes 612, 614 and 616 are used for measuring the voltage of the portion thereof which is touched by the user. The electrocardiogram signal processor 604 is coupled to the sensing electrodes 612, 614 and 616, and is used for processing the sensed voltage from the sensing electrodes 612, 614 and 616 and producing an ECG signal. Different from the "electrocardiogram signal sensing module 200" (which can work as a touchpad), the "electrocardiogram signal sensing apparatus 600" of the present invention does not have the touchpad area, but can be assembled with an independent touchpad or a touchpad area of any computer. In FIG. 6B, the touchpad 650 of the computer 690 has the same touch sensor 660, touchpad buttons 652, 654 and 656, and the touchpad controller 670. Different from the electrocardiogram signal sensing module 200, the electrocardiogram signal sensing apparatus 600 of the present invention will leave space for the touchpad 650 so that users can use the touchpad directly; and, the electrocardiogram signal sensing apparatus 600 comprises buttons 692, 694 and 696 (where the sensing electrode 612, 614 and 616 described above are mounted thereon), which can be respectively assembled with the touchpad buttons 652, 654 and 656 (shown by dot line) and be moved in unison with the buttons 652, 654, 656 at the same time when being pressed. In this embodiment, the transmission interface 630 can transmit the ECG signal produced by the electrocardiogram signal processor 604 to the touchpad 650 or the computer having the touchpad 650 through wired or wireless means.

In some embodiments, the electrocardiogram signal sensing module 200 or the electrocardiogram signal sensing apparatus 600 both comprises a storage medium (not shown in Figs.), which is used for recording and storing the obtained ECG signals when it is operated independently (without connection with other electrical devices such as computers). In some other embodiments, the electrocardiogram signal sensing module 200 or the electrocardiogram signal sensing apparatus 600 of the present invention may have a small-sized screen or indicating lights, for displaying or indicating the ECG signal and its related information. Those skilled in the art may use various memories, screens and indicating lights, and the various examples thereof will be omitted for brevity.

《The Computer Able to be Engaged with the Electrocardiogram Signal Sensing Apparatus Described Above》

The present invention further provides a computer (for example, the computer 690 shown in FIG. 6A). The computer 690 comprises a touchpad area 680, and the touchpad area 680 has the touch sensor which outputs a touch signal when being pressed by a user. In addition, the touchpad area 680 is able to be assembled with the electrocardiogram signal sensing apparatus 600 described above to sense the ECG signal. By combining the computer 690 and the electrocardiogram signal sensing apparatus 600 of the present invention, a user can use the touchpad and monitor his physical situation at the same time.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electrocardiogram (ECG) signal sensing module, comprising:
   a touchpad area;
   at least one touchpad button, for producing a press signal when being pressed, wherein the touchpad button is disposed on the touchpad area of a computer;
   at least one sensing electrode, mounted on the at least one touchpad button and moving in unison with the at least one touchpad button, for measuring the voltage on the portion thereof touched by a user;
   an electrocardiogram signal processor, coupled to the at least one sensing electrode, for processing the voltage on the at least one sensing electrode and producing an ECG signal; and
   a transmission interface, coupled to the at least one touchpad button and the electrocardiogram signal processor, for outputting the press signal and the ECG signal to the computer,
   wherein the touchpad area is an area on the computer that a user touches to move a cursor.

2. The electrocardiogram signal sensing module as claimed in claim 1, further comprising:
   a touch sensor, for producing a touch signal when being touched.

3. The electrocardiogram signal sensing module as claimed in claim 2, wherein the transmission interface is further coupled to the touch sensor for outputting the touch signal to the computer, wherein the touch sensor is disposed on the touchpad area.

4. The electrocardiogram signal sensing module as claimed in claim 2, further comprising a touchpad screen for displaying the electrocardiogram represented by the ECG signal.

5. The electrocardiogram signal sensing module as claimed in claim 1, wherein the transmission interface is wired.

6. The electrocardiogram signal sensing module as claimed in claim 1, wherein the transmission interface is wireless.

7. An electrocardiogram (ECG) signal sensing apparatus, configured to be assembled with a computer, comprising:
   a touchpad area;
   at least one touchpad button, wherein the at least one touchpad button is configured to be engaged with the touchpad area of the computer, wherein the touchpad area is an area on the computer that a user touches to move a cursor;
   at least one sensing electrode, mounted on the at least one touchpad button, for measuring the voltage thereof touched by a user;

an electrocardiogram signal processor, coupled to the at least one sensing electrode, for processing the voltage on the at least one sensing electrode and producing an ECG signal; and a transmission interface, coupled to the electrocardiogram signal processor, for outputting the ECG signal to a computer.

8. The electrocardiogram signal sensing apparatus as claimed in claim 7, further comprising:

a storage medium, for recording the ECG signal.

9. The electrocardiogram signal sensing apparatus as claimed in claim 7, further comprising:

a display, for displaying the ECG signal and related information.

10. The electrocardiogram signal sensing apparatus as claimed in claim 7, further comprising:

an indicating light, for indicating the ECG signal and the related information.

11. A computer, comprising:

a touchpad area, wherein the touchpad area is an area on the computer that a user touches to move a cursor;

an electrocardiogram signal sensing module, comprising:

a touch sensor disposed on the touchpad area, for producing a touch signal when being pressed;

at least one touchpad button, disposed on the touchpad area of the computer, for producing a press signal when being pressed;

at least one sensing electrode, mounted on the at least one touchpad button, for measuring the voltage on the portion thereof touched by a user; and an electrocardiogram signal processor, coupled to the at least one sensing electrode, for processing the voltage on the at least one sensing electrode and producing an ECG signal.

* * * * *